United States Patent [19]

Treutelaar

[11] 4,373,523
[45] Feb. 15, 1983

[54] HELMET MOUNTED CONSTANT TENSION TRACTION DEVICE

[76] Inventor: Edward J. Treutelaar, 8439 W. Sunnyside Ave., Chicago, Ill. 60656

[21] Appl. No.: 182,620

[22] Filed: Oct. 23, 1980

[51] Int. Cl.³ .......................................... A61M 15/08
[52] U.S. Cl. .............................................. 128/207.18
[58] Field of Search ............... 128/342, 344, 349 B, 128/349 BV, 246, DIG. 26, 207.18, 303 R

[56] References Cited

U.S. PATENT DOCUMENTS 4,018,221  4/1977  Rennie .................... 128/DIG. 26 X
4,083,369  4/1978  Sinnreich ........................ 128/344 X

*Primary Examiner*—Michael H. Thaler

[57] ABSTRACT

A helmet-type mounting for a constant tension traction device used for maintaining correct positioning of inserted esophageal varices tubes, with the device, when worn on the head, allowing complete mobility to the patient.

8 Claims, 7 Drawing Figures

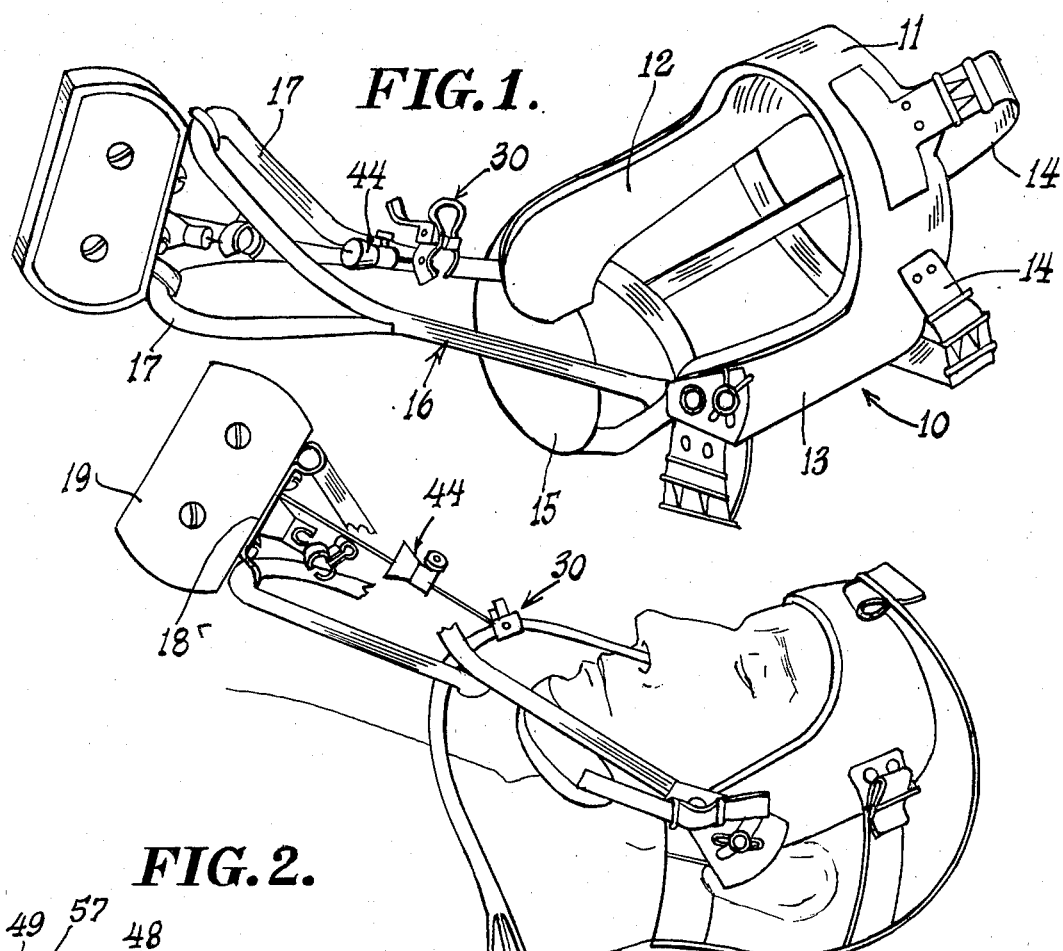
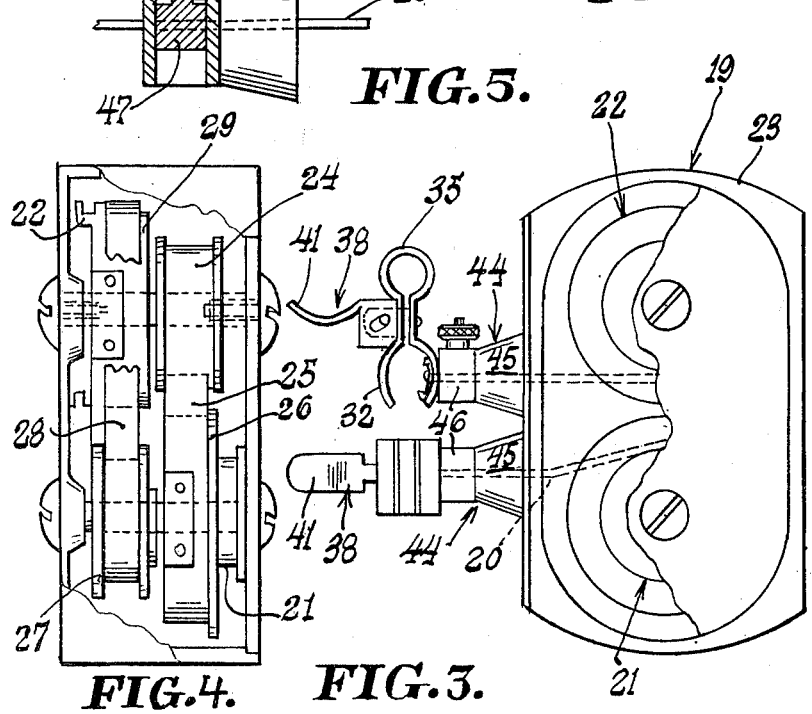
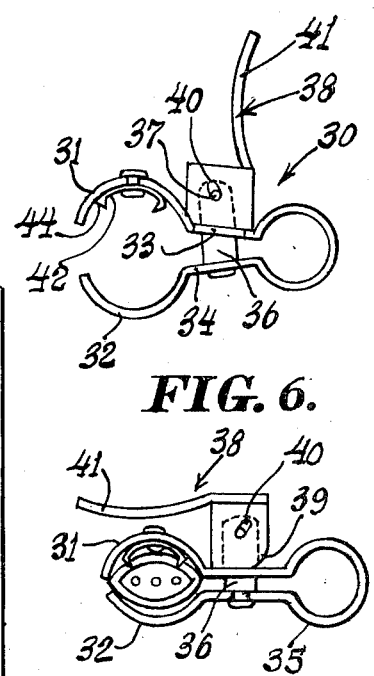

HELMET MOUNTED CONSTANT TENSION TRACTION DEVICE

SUMMARY OF THE INVENTION

The principal object of this invention is to provide an external constant tension traction device for use with inserted esophageal tubes.

In the treatment of internal bleeding from esophageal varices, a tube together with an inflatible balloon is inserted through the nostrils and the pharynx. The balloon is inflated, and it is of the utmost importance to maintain the same in an inflated position and under constant tension for the correct control of the internal bleeding.

The present invention is directed to an apparatus which has a helmet-type mounting on the head of a patient and which provides a constant tension traction upon the inserted esophageal varices tube, and which when in use does not interfere with the patient's mobility.

The present invention, while including a constant tension traction upon the esophageal varices tube, also includes a cam operated quick action clamping device for holding the tube in contact with the constant traction device without restricting or interfering with the esophageal varices tube.

The device of this invention is also provided with an adjustable stop, the purpose of which is to minimize the hazard of up-riding of the inserted tube so as to prevent disengagement of the gastric balloon from its inserted position.

A further object of the invention is to provide a constant tension traction device which is simple in its application and which is readily adaptable to accommodate various size patients and which is easily applicable in use and highly efficient in operation.

GENERAL DESCRIPTION OF DRAWING

The invention is best illustrated by the accompanied drawing showing the presented form of embodiment by which the objects of the invention are achieved and in which:

FIG. 1 is a perspective view of the device.

FIG. 2 is a perspective view of the device in place upon a patient.

FIG. 3 is a side elevational view of the constant tension traction device with a portion thereof broken away.

FIG. 4 is an end elevational view of the constant tension traction device with a portion thereof broken away.

FIG. 5 is a detailed sectional view of the adjustable stop utilized in the invention.

FIG. 6 is a plane view of the clamp used in the invention in an inoperative condition, and FIG. 7 is a plane view of the clamp utilized in this invention in its operative clamped position upon the esophageal varices tube.

GENERAL DESCRIPTION

To achieve the stated objects of the invention, I have provided a helmet-like structure 10 which includes a forehead rib 11 and integral cheek ribs 12 and 13. Adjustable cross head bands 14 as well as an adjustable chin strap 15 complete the structure of the helmet mounting.

Attached to the lower ends of the cheek ribs 12 and 13 is a U-shaped brace 16. The medial portion of the brace 16 is forked so as to provide a pair of supports 17. By means of a clamp 18, a constant tension device 19 is mounted upon the supports 17. The constant tension device 19 provides a set of cables 20 which are adapted to be wound about separate spools 21 and 22 located within the housing 23 of the constant tension device.

This constant tension device will embody the principles of operation and function of such a device as set forth in U.S. Pat. No. 3,085,768 dated Apr. 16, 1963. As such, the device consists of a reel 24 upon which is coiled a constant tensioning member in the form of a spring 25. The free end of the spring 25 is fixedly attached to a second reel 26 upon which is mounted one of the spools 21 for the cable 20. A second reel 27 is provided and it, too, has a spring 28, the free end of which is attached to a second reel 29, including the reel 22 for a second cable 20.

Each of the reels 24 and 27, together with their secondary reels 26 and 29 respectively, are of different diameters and therefore will effect different constant tension on the cables 20 as they pass from spools 21 and 22.

Adapted to be mounted on the free end of the wires 20 is a quick lock clamp 30 for the esophageal varices tube. The clamp 30 consists of a pair of curved jaws 31 and 32 carried at the ends of flat legs 33 and 34, which terminate into a spring bulb 35. An L-shaped flange 36 is fastened to the outer surface of the leg 34 and has a portion extending beyond the other leg 33 as seen in FIG. 6. Pivotally mounted on a pin 37 is a cam lock 38. The cam lock 38 is generally rectangular in shape and provides a curved cam corner edge 39. The pin 37 extends through a limited slot 40 formed in the cam lock 38 and is fixedly attached to the free exposed end of the flange 36. A finger tab 41 extends from one edge of the cam lock 38 and is used to facilitate the pivoting of the cam lock 38 about the pin 37 from the position shown in FIG. 6 to that shown in FIG. 7.

Within the curved jaw 31 is a gripping plate 42, having a set of prongs 43 struck therefrom. The plate 42 is preferably made from a semi-rigid material to that after connection to the jaw 31, the ends of the plate may be preset, by bending to receive tubes having variations in their diameters.

When the esophageal varices tube is placed within the jaws 31 and 32 of the clamp 30 and the cam lock 38 is pivoted as heretofor described, the prongs 43 will engage the external wall of the esophageal varices tube and will prevent slippage thereof through the clamp 30 without restricting the inner air tubes in the manner shown in FIG. 7.

Also positioned on each of the cables 20 is an adjustable stop 44. As viewed in FIG. 5, the stop 44 includes a circular conical bumper 45, as well as a hollow housing 46. Within the hollow housing 46 is a wedge lock 47 which provides a threaded shank 48 threadable through an opening 49 in the base wall 50 of the housing 46. The cable 20 is adapted to be freely journaled through suitable apertures formed in the bumper 45, opposite side walls of the housing 46, as well as through the wedge lock 47. A knurled head 57 is fastened to the shank 48 of the wedge lock 47, and thus by rotation thereof, the wedge lock 47 will be moved within the hollow housing 46 into a position that will bind the cable 20 between the wedge lock 47 and the inner side walls of the housing 46. Thus the stop 44 may be adjustably positioned at any point along the length of the cable 20.

As illustrated in FIG. 2, the helmet-like structure 10 has been placed upon the head of a patient. The esophageal varices tube has been inserted into the nostril of the patient and the tube is held in position by the clamp 30 and the constant tension traction unit 19. The adjustable stop 44 has been selectively positioned upon the cable 20 to minimize the hazard of upriding of the tube which could cause displacement of the same.

While the constant tension device 19 maintains the tube and balloon anchored in the gastric cardia of the patient by its pulling effect upon the cable 20, such tension must be arrested in the event that the balloon becomes disengaged in the gastric cardia such as by convulsions of the patient or if the balloon should burst. The arrest 44 will contact the front wall of the device 19 and only permit the small degree of upward pulling tension on the cable 20 preventing the dislocation of the balloon.

The foregoing device is adapted to be used with the esophageal varices tubes which include expandable balloons. The tube, together with both the esophageal varices balloon and gastric balloon is inserted through the nostril of a patient through the posterior pharynx and into the correct position for blocking the stomach tube. The balloons are then inflated and with a minimum of tension the tube is slightly withdrawn through the nose so as to properly place the inflated balloon in the desired position. It is the purpose of this invention to maintain the proper tension upon the tube so as to maintain the gastric balloon in proper position, while at the same time permitting passage of interior tubing which are used for further treatment of the patient.

While I have illustrated and described the preferred form of construction for carrying my invention into effect, this is capable of variation and modification without departing from the spirit of the invention. I therefore do not wish to be limited to the precise details of construction as set forth, but desire to avail myself of such variations and modifications as come within the scope of appended claims.

Having thus described my invention, what I claim as new and desire to protect by Letters Patent is:

1. A head-worn esophageal varices tube support having a constant tension traction device carried thereby and providing a connecting cable for attachment to the tube comprising:
   (a) a helmet-like structure to be worn on the head of a patient so as to allow full mobility for use,
   (b) a bracket extending forwardly from said helmet-like structure for mounting a constant tension traction device in a line substantially the continuation of the patient's nostrils,
   (c) a constant tension traction device mounted upon said bracket and providing a retractable cable,
   (d) means mounted on said cable of said constant tension traction device and releasably attached to the esophageal varices tube for mounting the same under constant tension after the same has been inserted in the nostrils of the patient, and
   (e) means adjustably fixed along the length of said cable to limit up-riding of the tube out of the patient's nostrils by said constant tension traction device.

2. A head-worn esophageal varices tube support as defined by claim 1 wherein said helmet-like structure comprises a forehead rib, cheek ribs and adjustable bands for mounting the same on the head of a patient.

3. A head-worn esophageal varices tube support as defined by claim 1 wherein said means mounted on the cable of the constant tension traction device for holding the esophageal varices tube under constant tension comprises a releasable clamp, said clamp consisting of a pair of curved jaws normally spring biased into an open position and a manually operable cam member for closing said jaws upon said esophageal varices tube.

4. A head-worn esophageal varices tube as defined by claim 3 wherein said helmet-like structure comprises a forehead rib, cheek ribs and adjustable bands for mounting the same on the head of a patient.

5. A head-worn esophageal varices tube support as defined by claim 4 wherein said helmet-like structure comprises a forehead rib, cheek ribs and adjustable bands for mounting the same of the head of a patient.

6. A head-worn esophageal varices tube support as defined by claim 1 wherein said means adjustably fixed along the length of the cable to limit up-riding of the tube comprises an adjustable stop, including a wedge lock for fixedly attaching the same, a preselected point along the length of the cable extending between the constant tension traction device and the esophageal varices tube.

7. A head-worn esophageal varices tube support as defined by claim 6 wherein said helmet-like structure comprises a forehead rib, cheek ribs and adjustable bands for mounting the same on the head of a patient.

8. A head-worn esophageal varices tube support as defined by claim 6 wherein said means mounted on the cable of the constant tension traction device for holding the esophageal varices tube under constant tension comprises a releasable clamp, said clamp consisting of a pair of curved jaws normally spring biased into a open position and a manually operable cam member for closing said jaws upon said esophageal varices tube.

* * * * *